US007776274B2

(12) United States Patent
Williamson, IV et al.

(10) Patent No.: US 7,776,274 B2
(45) Date of Patent: Aug. 17, 2010

(54) CASSETTE AND EMBEDDING ASSEMBLY FOR HANDLING AND HOLDING TISSUE SAMPLES DURING PROCESSING, EMBEDDING AND MICROTOME PROCEDURES, STAGING DEVICES THEREFORE, AND METHODS THEREFOR

(75) Inventors: Warren P. Williamson, IV, Loveland, OH (US); Craig B. Berky, Milford, OH (US); Stephen P. Whitlatch, Cincinnati, OH (US); Thomas J. Ward, Columbus, OH (US)

(73) Assignee: Biopath Automation, L.L.C., Loveland, OH (US)

( * ) Notice: Subject to any disclaimer, the term of this patent is extended or adjusted under 35 U.S.C. 154(b) by 1448 days.

(21) Appl. No.: 11/072,119

(22) Filed: Mar. 4, 2005

(65) Prior Publication Data
US 2005/0147538 A1 Jul. 7, 2005

Related U.S. Application Data

(63) Continuation of application No. PCT/US02/30775, filed on Sep. 26, 2002.

(51) Int. Cl.
*B01L 9/00* (2006.01)
(52) U.S. Cl. .............. 422/104; 422/102; 435/297.5
(58) Field of Classification Search .......... 422/102, 422/104; 435/297.5
See application file for complete search history.

(56) References Cited

U.S. PATENT DOCUMENTS

| 1,885,138 | A | 1/1932 | Pilson |
| 2,749,909 | A | 6/1956 | Ullery et al. ............. 128/2 |
| 2,776,596 | A | 1/1957 | Eigen |

(Continued)

FOREIGN PATENT DOCUMENTS

EP 0139424 A2 5/1985

(Continued)

OTHER PUBLICATIONS

Nicholas G. Genes et al., Effect of substrate mechanics on chondrocyte adhesion to modified alginate surfaces, Archives of Biochemistry and Biophysics 422 (2004) 161-167.

(Continued)

*Primary Examiner*—Lyle A Alexander
(74) *Attorney, Agent, or Firm*—Wood, Herron & Evans, L.L.P.

(57) ABSTRACT

The disclosure relates to a cassette, frame and mold for holding a tissue sample during an embedding and mircotoming process, and related methods. The cassette is sectionable in a microtome and includes a body with a bottom wall and a plurality of side walls. First and second side walls are generally V-shaped to present an apex of the "V" to the microtome blade. A lid of the cassette is stiffer than the bottom wall of the cassette to assist with positioning the tissue sample. The side walls of the cassette are perforated so as to significantly reduce the amount of cassette material that must be cut by the microtome blade. In one embodiment, to additionally reduce blade wear the ribs on one side wall are offset lengthwise relative to the ribs on an opposite side wall. An upper flange of the cassette includes depressions configured to register with detents in the frame.

8 Claims, 8 Drawing Sheets

U.S. PATENT DOCUMENTS

| | | | |
|---|---|---|---|
| 2,996,762 A | 8/1961 | McCormick | |
| 3,224,434 A | 12/1965 | Molomut et al. | 128/2 |
| 3,257,279 A | 6/1966 | Schain | 167/84.5 |
| 3,527,863 A | 9/1970 | Weichselbaum | 424/3 |
| 3,587,872 A | 6/1971 | Pauly | 214/1 |
| 3,624,197 A | 11/1971 | Schain | 424/3 |
| 3,679,450 A | 7/1972 | Reightol | 117/3 |
| 3,691,097 A | 9/1972 | Stiles et al. | 252/440 |
| 3,723,061 A | 3/1973 | Stahl | |
| 3,777,882 A | 12/1973 | McIntyre | |
| 3,814,670 A | 6/1974 | Freake et al. | 195/127 |
| 3,874,851 A | 4/1975 | Wilkins et al. | 23/230 |
| 3,961,097 A | 6/1976 | Gravlee, Jr. | 427/2 |
| 3,982,862 A | 9/1976 | Pickett et al. | 425/117 |
| 3,996,326 A | 12/1976 | Schachet | 264/158 |
| 4,025,306 A | 5/1977 | Studer | 23/230 |
| 4,199,558 A | 4/1980 | Henderson | 424/3 |
| 4,219,334 A | 8/1980 | Schluter et al. | 23/230 |
| 4,220,252 A | 9/1980 | Beall et al. | 220/307 |
| 4,224,277 A | 9/1980 | Macho et al. | 422/57 |
| 4,261,474 A | 4/1981 | Cohen | 215/250 |
| 4,340,066 A | 7/1982 | Shah | 128/749 |
| 4,353,856 A | 10/1982 | Mück et al. | 264/240 |
| 4,427,614 A | 1/1984 | Barham et al. | 264/210.1 |
| 4,435,507 A | 3/1984 | Stenkvist | 435/262 |
| 4,439,319 A | 3/1984 | Rock | 210/238 |
| 4,446,900 A | 5/1984 | Markovich | |
| 4,497,792 A | 2/1985 | Gindler | 424/3 |
| 4,545,831 A | 10/1985 | Ornstein | 156/57 |
| 4,557,903 A | 12/1985 | McCormick | 422/101 |
| 4,569,647 A | 2/1986 | McCormick | 425/117 |
| 4,576,796 A | 3/1986 | McCormick | |
| 4,627,129 A | 12/1986 | Wittes | |
| 4,656,047 A | 4/1987 | Kok et al. | 427/2 |
| 4,695,339 A | 9/1987 | Rada | 156/80 |
| 4,733,806 A | 3/1988 | Sloop | |
| 4,752,347 A | 6/1988 | Rada | 156/382 |
| 4,801,553 A | 1/1989 | Owen et al. | 436/174 |
| 4,817,631 A | 4/1989 | Schnepp-Pesch et al. | 128/753 |
| 4,820,504 A | 4/1989 | Battifora | 424/3 |
| 4,834,943 A | 5/1989 | Yoshiyama | |
| 4,839,194 A | 6/1989 | Malluche et al. | 427/2 |
| 4,849,173 A | 7/1989 | Chang | 422/56 |
| 4,870,975 A | 10/1989 | Cronk et al. | 428/749 |
| 4,887,612 A | 12/1989 | Esser et al. | 128/751 |
| 4,893,982 A | 1/1990 | Yamaguchi | 414/753 |
| 4,961,432 A | 10/1990 | Guirguis | 128/760 |
| 4,962,036 A | 10/1990 | Cermák et al. | 435/34 |
| 4,971,783 A | 11/1990 | Bolton et al. | 424/3 |
| 4,971,912 A | 11/1990 | Buhl et al. | 436/52 |
| 4,984,355 A | 1/1991 | Lubrano et al. | |
| 4,985,206 A | 1/1991 | Bowman et al. | 422/99 |
| 4,997,100 A | 3/1991 | Dudek | 220/306 |
| 5,002,184 A | 3/1991 | Lloyd | |
| 5,009,088 A | 4/1991 | Cislo | |
| 5,024,830 A | 6/1991 | Linner | 424/3 |
| 5,047,008 A | 9/1991 | de Juan, Jr. et al. | 604/22 |
| 5,057,546 A | 10/1991 | Sudan | |
| 5,077,012 A | 12/1991 | Guirguis | 422/58 |
| 5,080,869 A | 1/1992 | McCormick | 422/102 |
| 5,115,816 A | 5/1992 | Lee | 128/749 |
| 5,127,537 A | 7/1992 | Graham | |
| 5,132,758 A | 7/1992 | Minami et al. | 357/23.4 |
| 5,137,710 A | 8/1992 | Smalley et al. | 424/3 |
| 5,143,714 A | 9/1992 | Cosgrove et al. | |
| D330,257 S | 10/1992 | Schneider | |
| 5,170,800 A | 12/1992 | Smith et al. | 128/751 |
| 5,172,700 A | 12/1992 | Bencini et al. | 128/751 |
| 5,217,479 A | 6/1993 | Shuler | 606/180 |
| 5,224,488 A | 7/1993 | Neuffer | 128/751 |
| 5,272,093 A | 12/1993 | Silva et al. | |
| 5,284,753 A | 2/1994 | Goodwin, Jr. | 435/30 |
| 5,308,758 A | 5/1994 | Dahl | 435/30 |
| 5,312,758 A | 5/1994 | Ahlqvist | 436/63 |
| 5,318,589 A | 6/1994 | Lichtman | 606/205 |
| 5,340,551 A | 8/1994 | Berry, Jr. | |
| 5,350,150 A | 9/1994 | Fiore | |
| 5,354,370 A | 10/1994 | Schmehl | |
| 5,360,828 A | 11/1994 | Morrison | |
| 5,411,885 A | 5/1995 | Marx | |
| 5,427,742 A | 6/1995 | Holland | |
| 5,533,642 A | 7/1996 | Lafond et al. | |
| 5,586,438 A | 12/1996 | Fahy | |
| 5,609,827 A | 3/1997 | Russell et al. | |
| 5,650,327 A | 7/1997 | Copeland et al. | 436/46 |
| 5,665,398 A | 9/1997 | McCormick | 425/117 |
| 5,683,786 A | 11/1997 | Kavanaugh | |
| 5,702,185 A | 12/1997 | Heikal | |
| 5,718,916 A | 2/1998 | Scherr | |
| 5,817,032 A * | 10/1998 | Williamson et al. | 600/562 |
| 5,867,102 A | 2/1999 | Souder et al. | |
| 5,919,553 A | 7/1999 | Kavanaugh | |
| 5,928,934 A | 7/1999 | McCormick | 435/284.1 |
| 5,963,368 A | 10/1999 | Domanik et al. | |
| 5,968,436 A | 10/1999 | Takezaki | 264/250 |
| 6,017,476 A * | 1/2000 | Renshaw | 264/158 |
| 6,148,878 A | 11/2000 | Ganz et al. | |
| 6,193,102 B1 | 2/2001 | Bevirt et al. | |
| 6,207,408 B1 | 3/2001 | Essenfeld et al. | |
| D448,487 S | 9/2001 | Saez et al. | D24/216 |
| 6,289,682 B1 | 9/2001 | Rada | |
| 6,387,653 B1 | 5/2002 | Voneiff et al. | |
| 6,395,234 B1 | 5/2002 | Hunnell et al. | |
| 6,395,373 B2 | 5/2002 | Conti et al. | |
| 6,411,434 B1 | 6/2002 | Eastman et al. | |
| 6,486,783 B1 | 11/2002 | Hausladen et al. | |
| 6,489,171 B1 | 12/2002 | Aghassi et al. | |
| 6,495,104 B1 | 12/2002 | Unno et al. | |
| 6,498,032 B1 | 12/2002 | Clements et al. | |
| 6,513,673 B2 | 2/2003 | Alley | |
| 6,560,837 B1 | 5/2003 | Hodjat et al. | |
| 6,797,928 B2 | 9/2004 | Giberson et al. | |
| 7,005,110 B2 | 2/2006 | Taft et al. | |
| 7,156,814 B1 | 1/2007 | Williamson, IV et al. | |
| 7,179,424 B2 | 2/2007 | Williamson, IV et al. | |
| 2001/0000487 A1 | 4/2001 | Essenfeld et al. | |
| 2002/0030598 A1 | 3/2002 | Dombrowski et al. | |
| 2002/0196146 A1 | 12/2002 | Moore | |
| 2003/0021021 A1 | 1/2003 | Branch | |
| 2003/0119200 A1 | 6/2003 | Taft et al. | |
| 2003/0122673 A1 | 7/2003 | Anderson | |
| 2004/0032330 A1 | 2/2004 | Hoffman | |
| 2004/0203089 A1 | 10/2004 | Fischer | |
| 2005/0084425 A1 | 4/2005 | Williamson, IV et al. | |
| 2005/0100981 A1 | 5/2005 | Bjorsen | |
| 2005/0112034 A1 | 5/2005 | McCormick | |
| 2005/0137272 A1 | 6/2005 | Gaserod et al. | |
| 2005/0147538 A1 | 7/2005 | Williamson, IV et al. | |
| 2005/0226770 A1 | 10/2005 | Allen et al. | |
| 2007/0104618 A1 | 5/2007 | Williamson, IV et al. | |
| 2007/0116612 A1 | 5/2007 | Williamson, IV | |
| 2007/0166834 A1 | 7/2007 | Williamson, IV et al. | |
| 2008/0138854 A1 | 6/2008 | Williamson | |

FOREIGN PATENT DOCUMENTS

| | | |
|---|---|---|
| EP | 0142574 A1 | 5/1985 |
| EP | 0351988 A2 | 1/1990 |
| EP | 0357228 A1 | 3/1990 |
| EP | 0471534 A2 | 2/1992 |
| EP | 1321757 | 6/2003 |
| GB | 865889 A | 4/1961 |
| GB | 1483574 A | 8/1977 |
| GB | 2278441 A | 11/1994 |

| | | |
|---|---|---|
| JP | 62067424 | 3/1987 |
| JP | 11132923 A | 5/1999 |
| JP | 2001296220 A | 10/2001 |
| KR | 100458860 B1 | 11/2004 |
| WO | 8600407 A1 | 1/1986 |
| WO | 00/19897 * | 4/2000 |
| WO | 03040697 A1 | 5/2003 |
| WO | 2004028693 A1 | 4/2004 |
| WO | 2004029584 A1 | 4/2004 |
| WO | 205037182 A2 | 4/2005 |

OTHER PUBLICATIONS

U.S. Patent and Trademark Office, International Search Report in Corresponding PCT/US02/30779, Jan. 17, 2003, 3 pgs.

U.S. Patent and Trademark Office, International Preliminary Examination Report in Corresponding PCT/US02/30779, May 12, 2004, 3 pgs.

U.S. Patent and Trademark Office, Written Opinion in Corresponding PCT/US02/30775, Aug. 9, 2004, 6 pgs.

U.S. Patent and Trademark Office, International Preliminary Examination Report in Corresponding PCT/US02/30775, Oct. 28, 2004, 12 pgs.

U.S. Patent and Trademark Office, International Preliminary Examination Report in Corresponding PCT/US98/20478, Sep. 3, 1999, 3 pgs.

European Patent Office, Supplementary European Search Report in EP Application No. 98951995, Dec. 20, 2007.

U.S. Patent and Trademark Office, International Search Report and Written Opinion in PCT Application Serial No. PCT/US07/25253, Mar. 13, 2008.

European Patent Office, European Search Report in EP Application No. 06076973, Feb. 2, 2007.

European Patent Office, Supplementary European Search Report in EP Application Serial No. EP4794852, Apr. 21, 2008.

Sakura Finetek U.S.A. Inc., *Tissue-Tek® TEC™ 5*, Brochure, 2001.

Sakura Finetek U.S.A. Inc., *Tissue-Tek® VIP™ 5*, Brochure, 2001.

Japanese Patent Office, Office Action in Japanese Application No. 2004-539746, Aug. 1, 2007.

Japanese Patent Office, Office Action in Japanese Application No. 2004-539747, Jul. 24, 2007.

European Patent Office, Supplementary European Search Report in corresponding EP 02776027, Jul. 7, 2006.

European Patent Office, Supplementary European Search Report in EP Application No. 02773621, Sep. 2008.

Zebra's RFID Readiness Guide: Complying with RFID Tagging Mandates, Zebra Technologies, Jan. 2004.

Adding RFID Layer to Blood Safety Loop, CAP Today, Article, Jul. 2005, 6 pgs.

Bar Coding for Patient Safety, The New England Journal of Medicine, 353; 4, Jul. 28, 2005.

The Latest in Products and Services, Bar Coding/RFID, www.healthcare-informatics.com, Nov. 2005.

U.S. Patent and Trademark Office, International Preliminary Examination Report in corresponding PCT Serial No. PCT/US04/33604, May 8, 2006.

U.S. Patent and Trademark Office, International Search Report and Written Opinion in corresponding PCT Serial No. PCT/US04/33604, Nov. 15, 2005, 13 pgs.

European Patent Office, European Search Report in EP Application No. 08013740, Oct. 23, 2008.

U.S. Patent and Trademark Office, Office Action in U.S. Appl. No. 11/010,773, Apr. 2, 2009.

U.S. Patent and Trademark Office, Office Action in U.S. Appl. No. 11/553,120, Apr. 10, 2009.

* cited by examiner

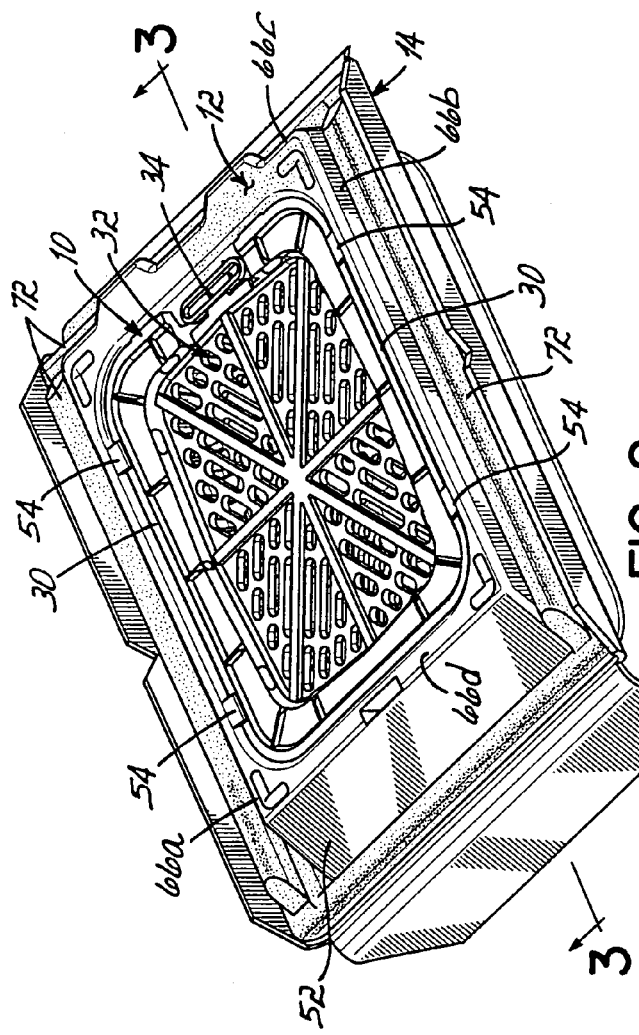
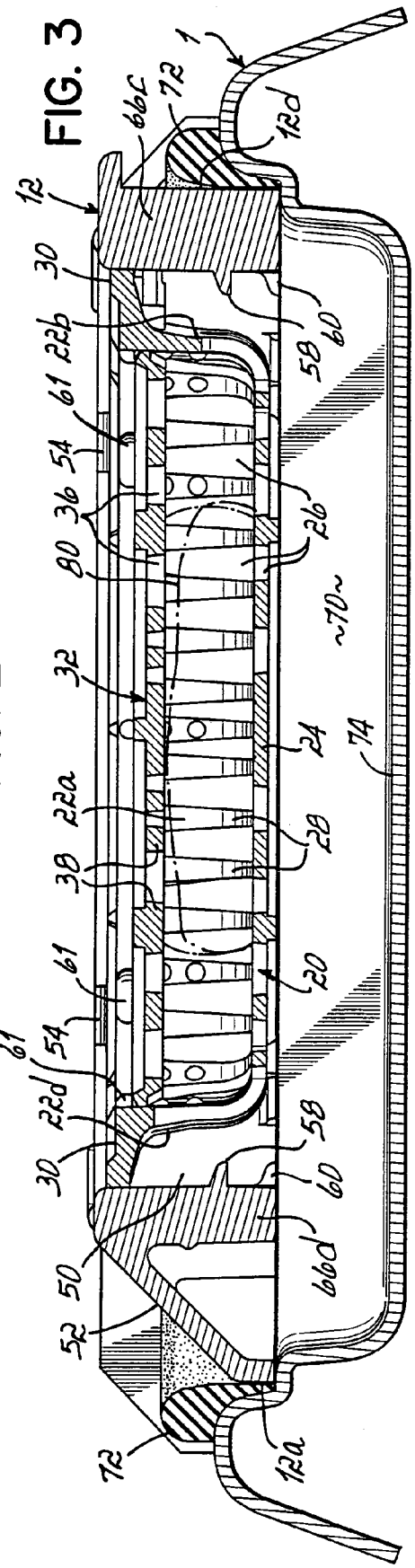
FIG. 2
FIG. 3

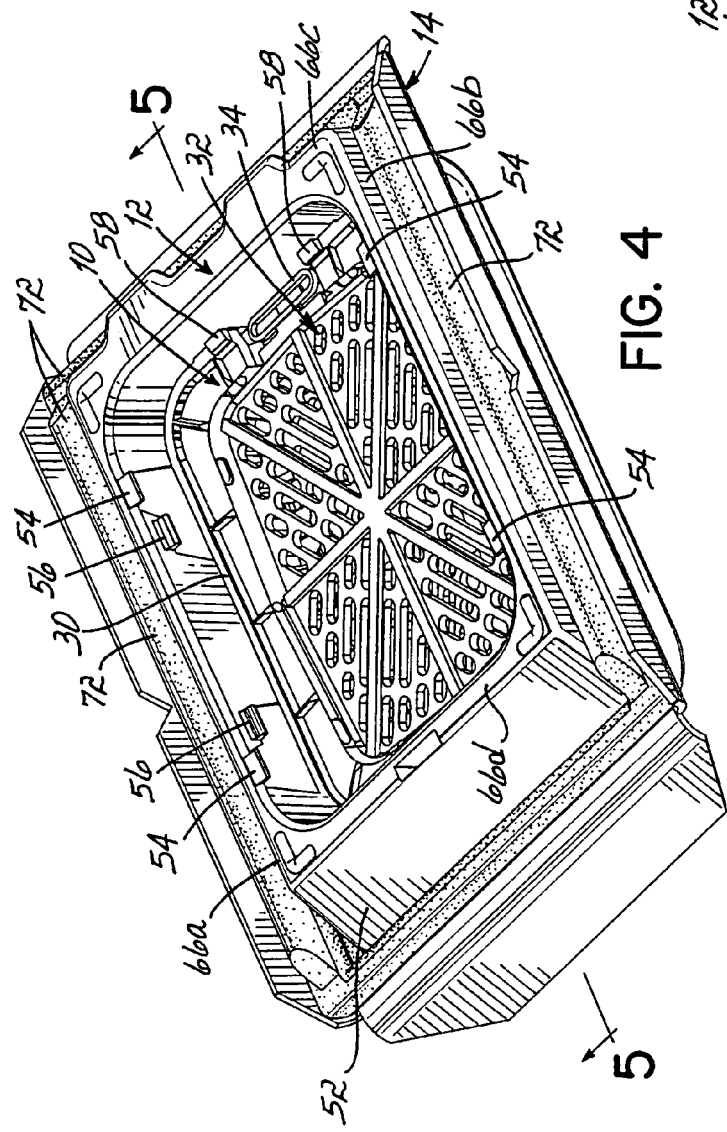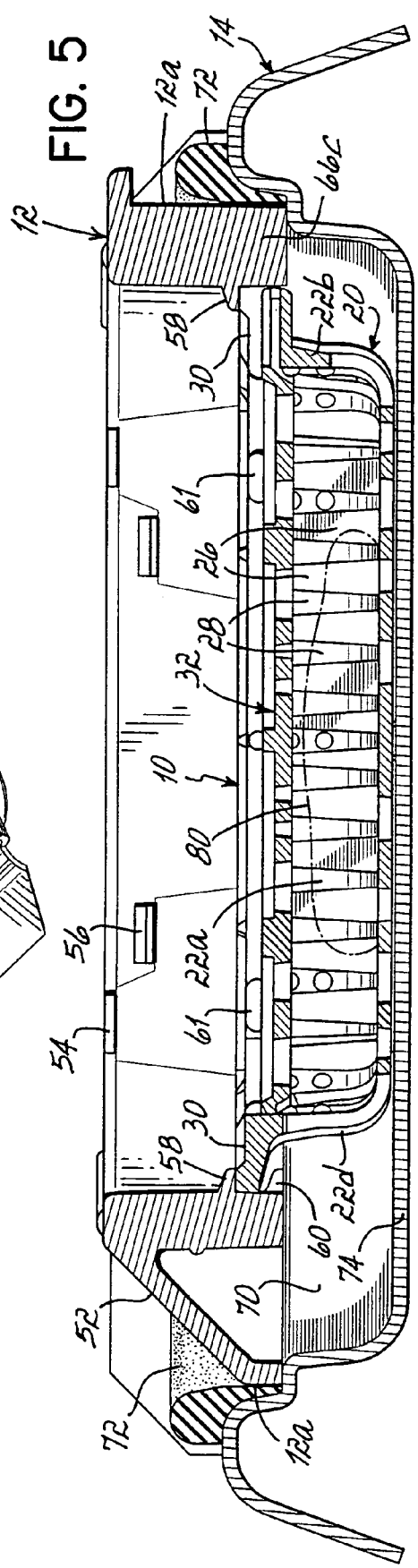

CASSETTE AND EMBEDDING ASSEMBLY FOR HANDLING AND HOLDING TISSUE SAMPLES DURING PROCESSING, EMBEDDING AND MICROTOME PROCEDURES, STAGING DEVICES THEREFORE, AND METHODS THEREFOR

The present application is a continuation of PCT Serial No. PCT/US02/30775 filed on Sep. 26, 2002 (now pending), the disclosure of which is hereby fully incorporated by reference herein.

FIELD OF THE INVENTION

The present invention generally relates to supports for handling and embedding tissue samples for pathological analysis and, more particularly, to cassettes which can receive one or more tissue samples and be embedded and subsequently microtomed with the tissue sample or samples.

BACKGROUND OF THE INVENTION

To accurately diagnose various tissue diseases and conditions, medical personnel must remove one or more samples of tissue from the body of a patient. This process of harvesting tissue from the body is known as a biopsy. Once the tissue sample or samples are removed and sent to a pathology laboratory, the tissue will go through a series of procedures performed by a histotechnician and, ultimately, a pathologist, in order to diagnose the tissue. The present invention generally relates to those procedures that are normally performed by the histotechnician to prepare the tissue sample or samples into slides that may be analyzed under a microscope by the pathologist.

Although the singular term "sample" is used throughout this specification, it should be understood that this term likewise encompasses plural "samples" as well. Once a tissue sample is removed from the body of a patient, it is typically placed into a specimen container containing a tissue fixative solution and then the container is transported to a pathology laboratory. The tissue will undergo a process known as "grossing-in" in the pathology lab during which a histotechnician will retrieve the tissue sample from the container, typically cut the tissue into appropriate sizes for tissue processing, place individual samples into the appropriate sized small plastic tissue cassettes, and assign tracking numbers to each cassette. These tracking numbers are then logged into a tracking system used in the laboratory. For the smallest tissue samples, which may only be scrapings, the cassette will have fine mesh openings on the sides and bottoms. In other situations involving very small tissue samples, the samples are placed into a bag that resembles a tea bag and prevents the smallest tissue samples from escaping. Larger tissue samples are placed into cassettes having somewhat larger slotted openings which are again smaller than the tissue sample inside the cassette.

The cassettes are then placed into a stainless steel perforated basket and run through a tissue processing machine, often overnight. This machine uses a combination of vacuum, heat, and chemicals to remove the interstitial fluids. Once the fluids have been removed from the tissue samples, the processing machine immerses the tissues samples in a bath of molten paraffin so that the interstices in the tissue are replaced with paraffin. The histotechnician then removes the basket from the machine and removes the individual tissue cassettes. At an embedding station, which has a molten paraffin reservoir and dispenser, the histotechnician will individually remove the tissue from each cassette. The histotechnician must carefully orient the tissue sample, based on tissue type, into a stainless steel base mold which is roughly the size of the tissue cassette and is partially filled with molten paraffin. The tissue sample must be manually held, typically using forceps, against the bottom of the mold. If it is not, this could compromise the ability to make proper slices of the tissue later in the microtome. The molten paraffin is then rapidly cooled on a refrigerated plate, which may be a thermal electric cooler (TEC), to partially solidify the paraffin thereby holding the tissue sample in the proper orientation against the bottom of the mold. The cassette is then placed on top of the base mold and paraffin is poured through the opened top of the cassette into the base mold. The cassette changes its function at this point in the procedure from a tissue holding component to a fixation device for later use in taking shavings or slices from the solidified paraffin in a microtome. The base mold is chilled until all of the molten paraffin has solidified and the histotechnician removes the stainless steel base mold from the block of embedded paraffin. The tissue sample is thus embedded within a rectangular block of paraffin with a plastic tissue cassette on the opposite side which will then be used as a holder in the chuck of the microtome. As with the tissue processing machine, the embedding process is accomplished in a batch fashion during which an average histotechnician may embed approximately 40 to 60 cassettes per hour.

The blocks of hardened paraffin containing the embedded tissue samples are then ready to be sliced into extremely thin sections for placement on a microscope slide. The histotechnician mounts the embedded tissue block in a chuck on the microtome which is sized to accept the side of the block that has the embedded plastic cassette. The histotechnician can then begin slicing the paraffin block which has the tissue sample embedded opposite to the plastic cassette surface. This yields a ribbon of individual slices of the tissue embedded in the paraffin. The action of the microtome causes the individual slices to stick together when done properly and, subsequently, these very thin ribbons of slices are floated into a water bath and a glass slide is carefully placed underneath the slice. The slice, with the thin sectioned tissue sample embedded therein, is then adhered to the top of the slide.

When the histotechnician has enough slides from the tissue sample, the slides are placed into an automatic staining machine. The staining machine goes through a series of infiltrating steps to stain the different tissue and cells of the slide different colors. This helps the pathologist identify different structures and makes it easier to find any abnormalities in the tissue. After the staining procedure is complete, the slides are cover slipped and prepared for the pathologist to place under a microscope to analyze.

Based on the summary of the procedure provided above, it will be appreciated that conventional tissue sample handling and processing is a very labor-intensive process involving several manual steps performed by a histotechnician. Thus, repetitive stress injuries such as carpal tunnel syndrome are prevalent. This is especially true with the tissue sample embedding process. These multiple manual operations and repeated tissue handling increase the likelihood of human error and, moreover, require highly trained and skilled histotechnicians to ensure that the tissue samples ultimately adhered to the slides for analysis by the pathologist are in an optimum condition and orientation to make accurate diagnoses.

U.S. Pat. No. 5,817,032 (the '032 patent) discloses various improvements to this area of technology, including new manners of holding tissue samples during the grossing in, embedding, and microtome or slicing procedures. More specifically, the '032 patent relates to a tissue trapping and supporting device, which may be a cassette, and which may be cut with a microtome. When a cassette is used, the tissue sample is immobilized within the cassette and subjected to the process for replacing tissue fluids with paraffin. Then, the tissue sample and the cassette are sliced at the same time for mounting on microscope slides. Because the tissue sample is never removed from the cassette from the time it is processed in the tissue processing machine to the time that it is cut with the microtome, a significant amount of handling time is saved. Moreover, the chance for human error or tissue loss due, for example, to dropping the tissue during handling, is significantly reduced due to the elimination of separate tissue handling steps. This patent also generally discusses an automated process which, in conjunction with the novel tissue cassettes, even further reduces the handling steps during the entire procedure.

In spite of the various advances made in this field, there is an increasing need for additional improvements related to increased production capability and increased and more consistent quality of embedded tissue samples and resulting slices or ribbons of embedded tissue which will be subject to diagnosis.

SUMMARY OF THE INVENTION

Generally the invention relates to a cassette for holding a tissue sample during an embedding and microtoming or slicing process. The cassette includes a body with a bottom wall and a plurality of side walls extending upwardly with respect to the bottom wall to define an interior space for receiving the tissue sample. The bottom wall and the plurality of side walls are constructed of a material capable of being sectioned in a microtome. Preferably, the cassette material is also resistant to any type of degradation during processing which would compromise its ability to function in accordance with the invention. In a first aspect of the invention, the plurality of side walls comprise first and second side walls on opposite sides of the bottom wall each including portions angling from approximate midpoints of the first and second side walls toward the other of the first and second side walls on the opposite side of the bottom wall. In the preferred embodiment, the two longest side walls of the four side walls comprising a rectangular cassette are generally V-shaped in a direction away from the interior of the cassette. This presents an apex of the V-shape to the microtome blade, after the embedding process is complete, which assists with the cutting action. Specifically, this feature has been found to reduce or prevent the hardened paraffin from breaking or cracking away from the cassette side wall material while making slices in the microtome.

The cassette preferably further includes a lid configured to be coupled with the body for movement between open and closed positions. The lid may be depressed downwardly on top of the tissue sample in the cassette interior. The lid is preferably stiffer than the bottom wall of the cassette. This feature allows the lid to position the tissue sample in the cassette parallel to the bottom of the mold during the embedding process. More specifically, the stiffer lid pushes the tissue sample and the more flexible bottom wall of the cassette against the rigid bottom of a base mold while the molten paraffin solidifies. This helps ensure that the bottom wall of the cassette can be removed in its entirety during a facing operation in the microtome prior to slicing the tissue sample, and that the tissue is positioned flatly against the bottom wall of the cassette.

In another aspect of the invention, the side walls of the cassette are perforated such that there is at least a ratio of about 2.5:1 of open area to solid material area whereby the solidified paraffin occupies the open area of the side walls. This ratio may be altered by using different materials for the cassette and/or paraffin embedding media. For instance, a higher molecular weight paraffin or lower moneluculer weight cassette will allow the ratio to vary somewhat. Currently, an industry standard paraffin (e.g., Sakura VIP processing/embedding medium) works best with a ratio of at least about 3.0:1 and, more preferably, at least about 3.5:1. This reduces the amount of cassette material that must be cut by the microtome blade while taking slices of the tissue and, therefore, increases blade life and quality of the resulting ribboned, embedded tissue samples. In addition this ratio assures that the paraffin is strong enough not to fracture when cut by the microtome blade. Another feature that results in similar advantages involves forming the side walls from ribs and offsetting the ribs of one of the first and second side walls with respect to those of the opposite side wall along the side wall length. Thus, the microtome blade will contact a more uniform amount of the cassette material along its length during each pass. This significantly reduces blade wear while cutting through the cassette material. Reduced blade wear is advantageous to keeping blade costs under control as the majority of blades used are disposable.

In another aspect of the invention, the cassette further includes a flange extending along upper portions of at least two of the side walls. The flange includes depressions configured to register with detents in a frame during the tissue embedding process. This increases the effective height dimension of the cassette interior, thereby allowing more tissue to be placed in the cassette and more passes to be made in the microtome. In this regard each pass of the microtome may only take a 5 micron slice. Therefore, using depressions having a depth, for example, of 0.14" can allow about 70 more slices to be taken in the microtome.

The invention further contemplates the various unique assemblies of two or more of the tissue cassette, frame, and base mold as disclosed herein. With respect to the frame and base mold, for example, structure is provided to physically hold the frame against the base mold. In the preferred embodiment, a seal is provided to perform this holding function and also to prevent leakage of liquid paraffin from the base mold.

In another aspect, the invention contemplates a device for staging a tissue sample cassette from an upper position in a frame used during a tissue embedding process to a lower position in the frame. The device includes a handle, a staging mechanism coupled with the handle and configured to engage an upper surface of the cassette, and a stop operatively coupled to the handle and configure to stop vertical movement of the staging mechanism when the cassette reaches the lower position in the frame. The staging mechanism further comprises a plurality of fingers which are configured to engage a corresponding plurality of locations on the upper surface of the cassette. For example, four fingers may be provided for engaging four corner locations on the cassette. This helps ensure that the cassette is engaged with at least four pairs of detents located proximate corner portions of the cassette thereby positioning the bottom wall of the cassette parallel to and against the bottom wall of the base mold.

In one embodiment, the staging device is a rigid member and the stop comprises a fixed stop member coupled for movement with the staging mechanism and configured to stop against an upper surface of the frame. In another embodiment, the device includes a stabilizing mechanism coupled with the handle and moveable relative to the staging mechanism. The stabilizing mechanism is configured to engage an upper surface of the frame as the staging mechanism moves the cassette from the upper position to the lower position within the frame. In this embodiment, the staging mechanism is normally spring-biased into an upward position and is forced downward against the spring bias when moving the cassette from the upper position to the lower position. The stop in this embodiment further comprises respective surfaces of the handle and stabilizing mechanism which engage one another when the staging mechanism has placed the cassette into the lower position. The staging devices of this invention ensure that the cassette is fully staged into the base mold, while ensuring that the cassette is not pushed too far through the frame. Moreover, the staging devices ensure that the bottom wall of the cassette and, therefore, the tissue sample, lay flat against the bottom of the base mold. This improves the efficiency and quality of tissue shavings later made in the microtome.

The invention also encompasses the various methods of using the tissue cassette and cassette/frame/base mold assemblies as disclosed herein.

These and other objects, advantages, and features of the invention will become more readily apparent to those of ordinary skill in the art upon review of the following detailed description taken in conjunction with the accompanying drawings.

BRIEF DESCRIPTION OF THE DRAWINGS

FIG. 2 is an assembled perspective view of the tissue cassette, frame and base mold.

FIG. 3 is a cross sectional view taken along line 3-3 of FIG. 2 and showing the tissue cassette in its initial upper position.

FIG. 4 is an assembled perspective view, similar to FIG. 2 but illustrating the second, staged position of the tissue cassette.

FIG. 5 is a cross sectional view taken along line 5-5 of FIG. 4 and showing the tissue cassette staged down into its second, lower position against the bottom of the base mold.

DETAILED DESCRIPTION

Figure 1:
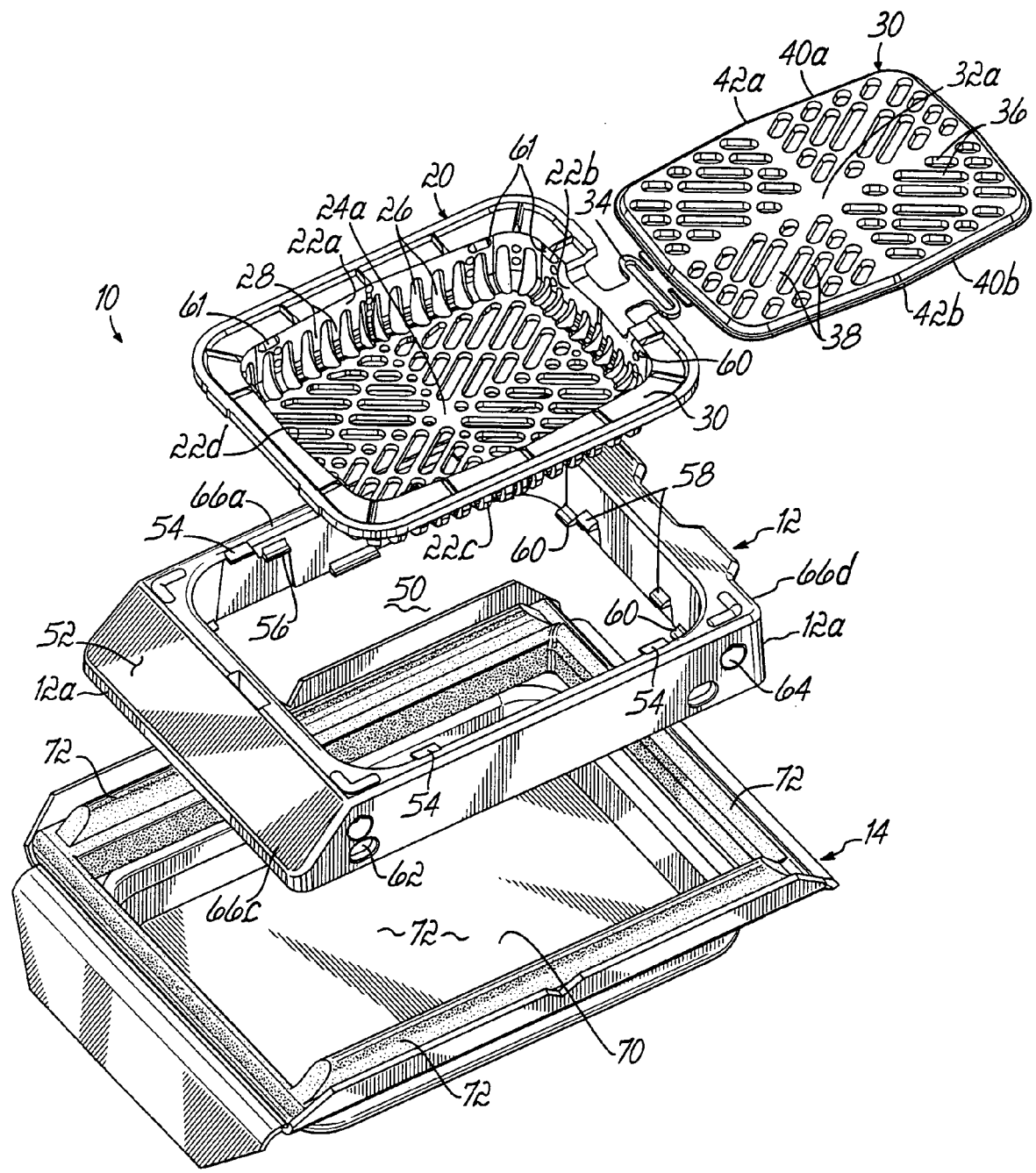
FIG. 1 is an exploded perspective view of an assembly including the tissue cassette, the frame into which the cassette is inserted and the base mold into which the frame and cassette assembly are inserted.

Turning first to FIGS. 1-3, a tissue cassette 10 constructed in accordance with the invention is received within a frame 12 and the tissue cassette 10 and frame 12 are then positioned in a base mold 14. After a staging operation the base mold 14 is subsequently filled with liquid paraffin, as described further below. Tissue cassette 10 includes a perforated body 20 formed by four side walls 22a, 22b, 22c, 22d and a bottom wall 24. Each wall is preferably constructed with perforations or openings 26 and ribs 28. An upper flange 30 surrounds and extends outwardly from the respective side walls 22a-d. A lid 32 is attached to body 20 by a hinge 34 which allows vertical movement of lid 32 into the interior of body 20 for retaining one or more tissue samples against bottom wall 24. Lid 32 is likewise formed with perforations 36 which may be elongated and generally separated by ribs 38. As shown best in FIG. 1, elongated perforations 26, 36 on the bottom wall 24 and lid 32 respectively extend toward central areas 24a, 32a of the bottom wall 24 and lid 32. This assists with allowing a mold (not shown) to fill with material, such as PFA, during the molding process of cassette 10.

Lid 32 is formed with a shape along its circumference which compliments the shape of side walls 22a-d. In this regard, respective lengthwise side edges 40a, 40b of lid 32 are formed in the shape of a shallow "V" and each includes an apex 42a, 42b generally at the central portion thereof. This likewise corresponds to the lengthwise shallow "V" shape of side wall 22a and opposite side wall 22c. Thus, when the embedded tissue cassette is later placed in a microtome and sections are sliced from the embedded tissue cassette, the microtome blade will initially contact the apex corresponding of side wall 22a or 22c, depending on which side is facing up in the microtome. This has been found to increase the quality of ribboned slices being made from the embedded tissue cassette. That is, little or no fracturing of paraffin will occur at the paraffin/cassette interfaces.

Frame 12 more specifically includes an open interior 50 which receives cassette 10, and an angled front wall 52 which may be used for recording indicia, such as patient data. Respective upper and lower sets of detents 54, 56 and 58, 60 extend inwardly into the open interior 50 of frame 12. Initially, tissue cassette 10 is held between the upper pairs of detents 54, 56 by pressing the upper flange 30 downwardly past the upper sets of detents 54 and against the lower set of detents 56 after one or more tissue samples have been placed into cassette body 20 and lid 32 has been closed. Respective detents 61 extend inwardly from side walls 22a-d to allow lid 32 to be snapped and retained in a closed position. During a staging operation, tissue cassette 10 will be moved vertically downwardly through frame 12 until flange 30 snaps past detents 58 and rests against detents 60 at a lower position (FIG. 5). Recesses 62, 64 are formed in at least two opposite side walls for allowing fingers of a gripper mechanism to register with the assembly during automated handling and embedding operations, as necessary. Preferably side walls 66a, 66b contain these recesses 62, 64, while additional side walls 66c, 66d may include additional structure allowing automated handling, or allowing other functions as necessary. Base mold 14 includes an open interior 70 for receiving frame 12 and may be surrounded by a resilient elastomeric seal 72 which prevents the escape of liquid paraffin during the embedding process. This eliminates an additional step of scraping off excess hardened paraffin from frame 12 after the embedding process is complete. Such excess paraffin can prevent the frame from properly fitting in a microtome chuck.

Figure 6:
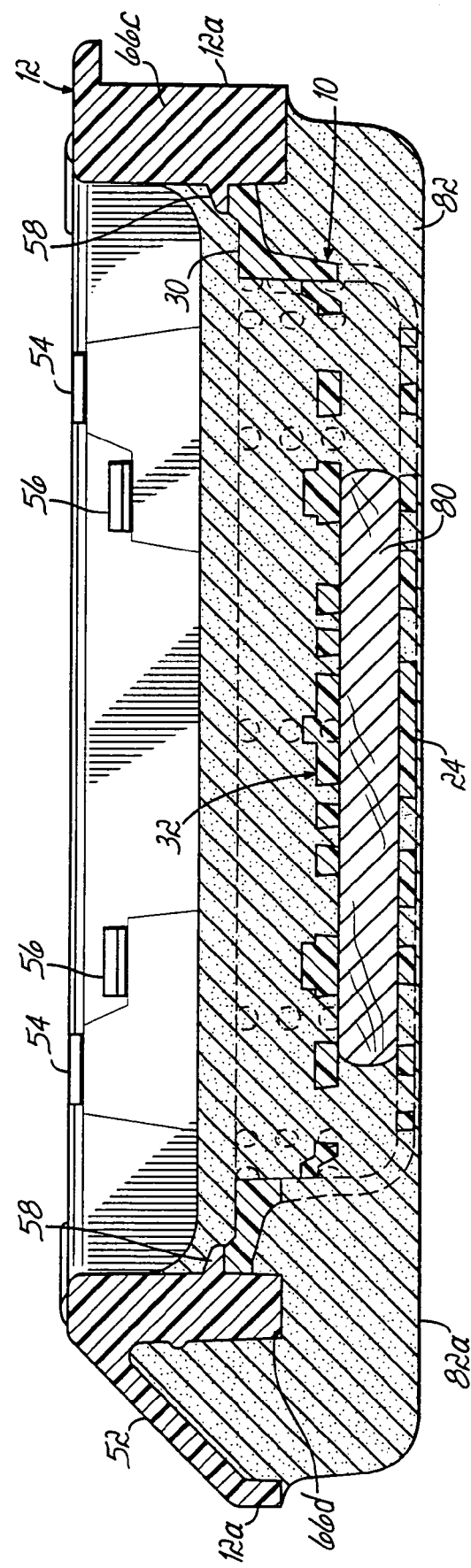
FIG. 6 is a cross sectional view of the frame and the tissue cassette embedded in material such as paraffin, after release from the base mold.

By comparing FIGS. 2 and 3 to FIGS. 4 and 5, it will be appreciated that during the staging process, tissue cassette 10 is moved vertically downward into the interior 70 of base mold 14 such that the bottom 24 of tissue cassette 10 contacts the bottom 74 of base mold 14. At this position, flange 30 of tissue cassette body 20 is received between respective detents 58, 60 holding it in this lower position. Frame 12 is preferably press fit and held frictionally within base mold 14 by one or more resilient seals 72. Seal 72 performs two functions in this embodiment. First, it physically holds frame 12 within base mold 14 by friction. This prevents the frame 12 and attached cassette 10 from floating or otherwise moving while base mold 14 is filled with paraffin. Second, it prevents the liquid paraffin from escaping from base mold 14 in the area between outer walls 12a of frame 12 and interior 70 of base mold 14. It will be appreciated that a holding member other than seal 72 may be used instead to physically hold frame 12 against base mold 14. In this case, seal 72 may not be necessary. As some examples, such holding members may be clamps, fasteners, spring members or weights. In these figures, the tissue sample or samples within cassette 10 have been deleted for clarity. However, it should be understood, that lid 32 will be depressed down onto one or more tissue samples 80 contained with the interior of cassette body 20 (FIG. 6). While the assembly of cassette 10, frame 12 and base mold 14 is in the staged configuration shown in FIGS. 4 and 5, liquid paraffin is introduced through the open interior of frame 12 and through the perforations 26, 36 of cassette 10 into the interior 70 of base mold 14. The liquid paraffin is then preferably cooled on a suitable cooling device, such as a TEC, and the assembly of the tissue cassette 10, frame 12, embedded tissue sample 80 and hardened paraffin 82 is removed from base mold 14 as shown in FIG. 6. Frame 12 may then be used as a device to fix the assembly in a microtome chuck and slices are then taken from the bottom surface 82a of paraffin 82. Initially, a facing blade is used to remove the initial layer of paraffin 82 and bottom wall 24 of tissue cassette 10. At this point, a different microtome blade may be used to take ribboned slices or shavings of tissue sample 80 and the surrounding paraffin 82 and side walls 22a-d of tissue cassette body 20. Often times the same blade that is used for facing may also be used for sectioning.

Figure 7:
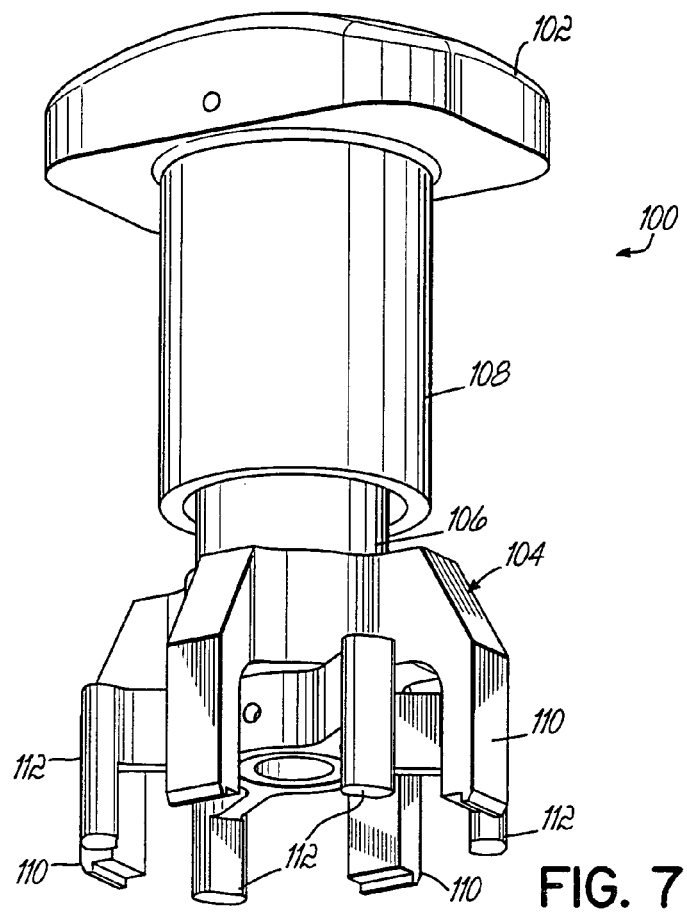
FIG. 7 is a perspective view of a manual, spring-biased staging device.
Figure 8:
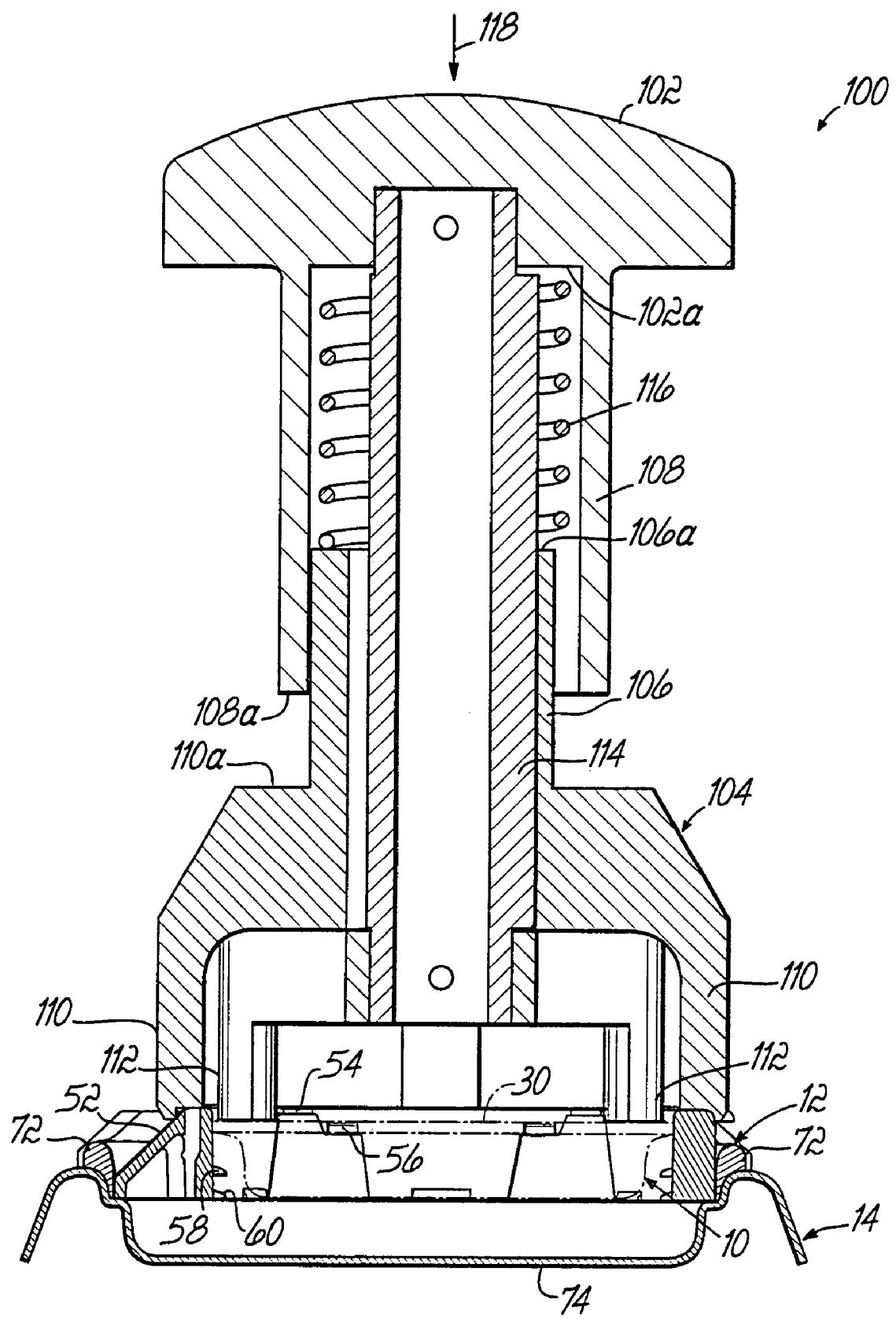
FIG. 8 is a longitudinal cross sectional view of the staging device of FIG. 7 being used to stage a tissue cassette through the frame and into the base mold.

FIGS. 7 and 8 illustrate one type of staging device 100 which may be used in conjunction with the tissue cassette 10, frame 12 and base mold 14 described above. Staging device 100 includes a handle 102 at an upper end and a staging mechanism 104 at a lower end. Staging mechanism 104 is coupled to a hollow cylinder 106 extending upwardly into a shroud 108 rigidly connected with handle 102. A plurality of four stabilizer members 110 are rigidly coupled with cylinder 106, while a plurality of preferably movable staging fingers 112 are coupled to a reciprocating shaft 114 which extends through cylinder 106. Shaft 114 is rigidly connected to handle 102 and is biased therewith in an upward position by a spring 116 positioned between a bottom surface 102a of handle 102 and an upper surface 106a of cylinder 106. Thus, it will be appreciated that stabilizer members 110 may be placed against an upper side of frame 12 for stabilizing purposes and handle 102 may then be depressed downwardly as indicated by arrow 118. This moves reciprocating shaft 114 and the attached staging fingers 112 downwardly against tissue cassette 10 thereby moving the tissue cassette 10 relative to frame 12 from its upper position shown in FIG. 3 to its lower, staged position shown in FIG. 5. To avoid pushing cassette 100 too far through frame 12, surface 108a stops against surface 110a as flange 30 reaches its lower position between detents 58, 60.

Figure 10:
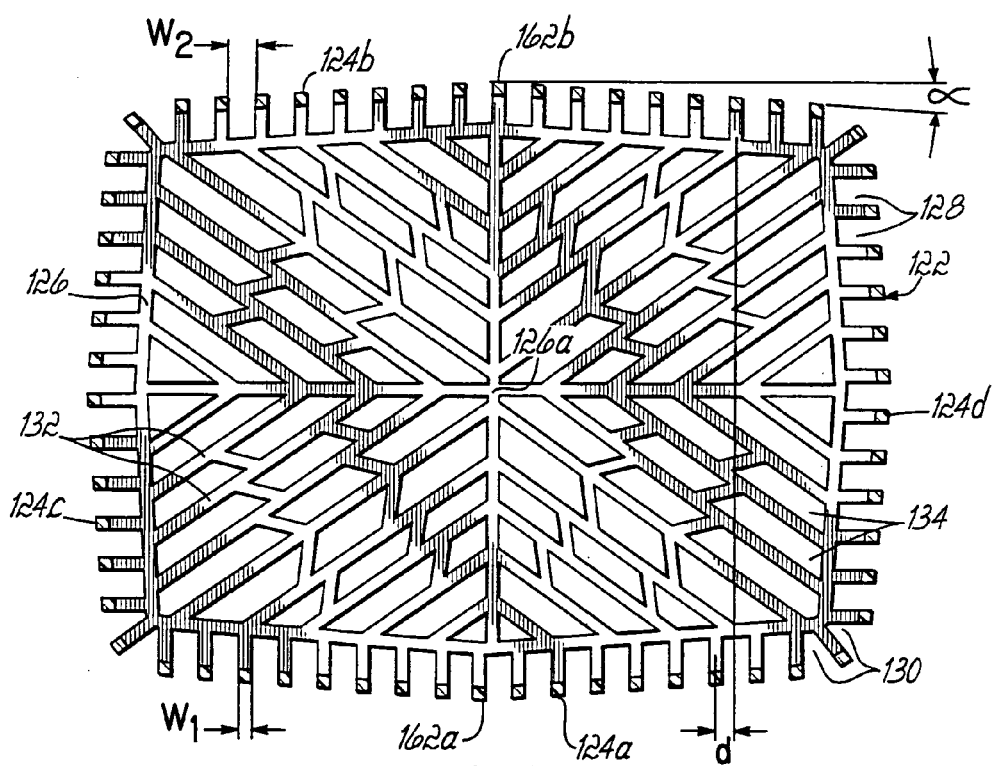
FIG. 10 is a cross sectional view taken along line 10-10 of FIG. 9.
Figure 9:
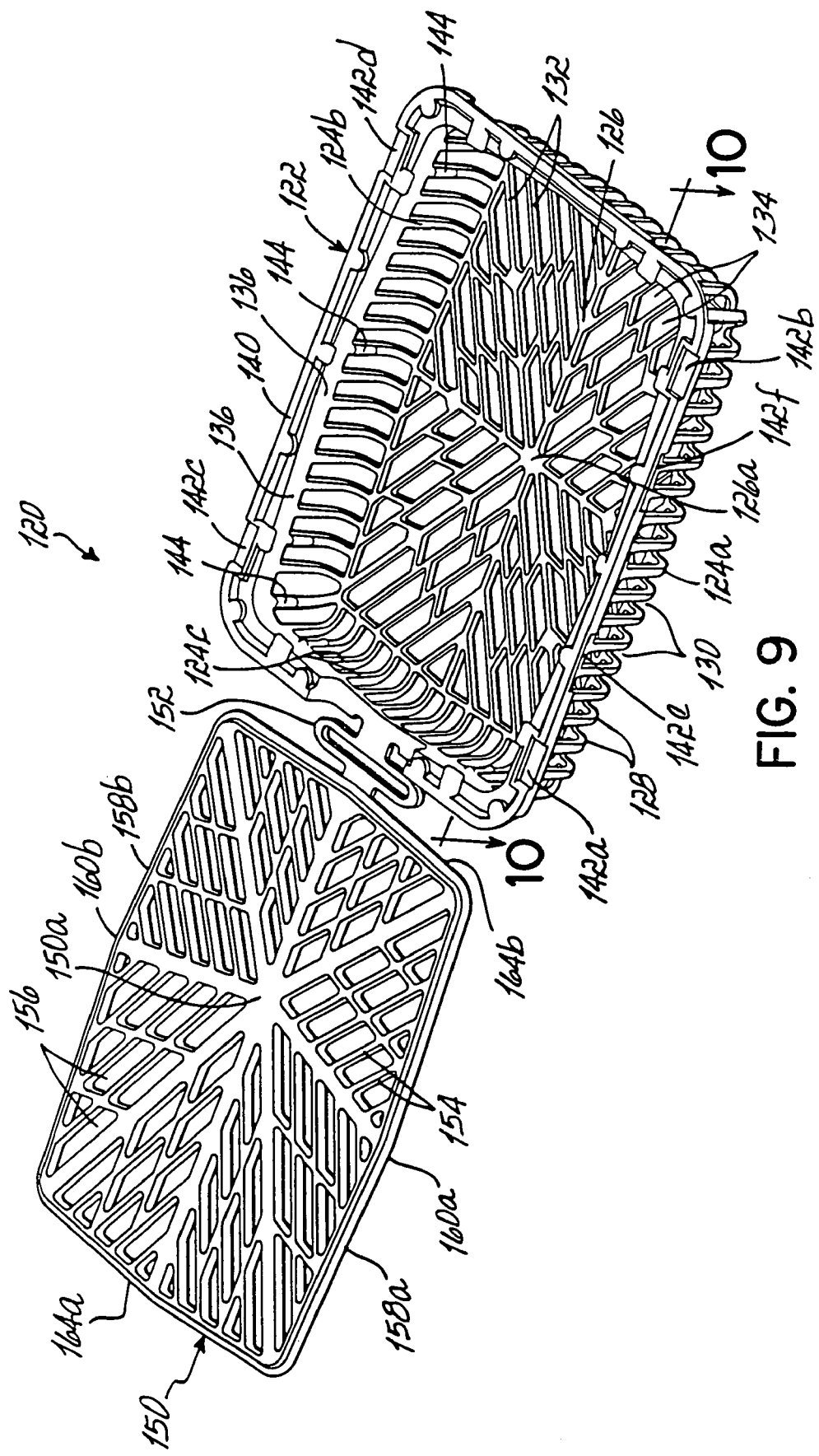
FIG. 9 is a perspective view of a tissue cassette constructed in accordance with a second embodiment of the invention.

FIGS. 9 and 10 illustrate a second embodiment of a tissue cassette 120. Tissue cassette 120 includes a cassette body 122 having four side walls 124a-d surrounding an open interior and bounded on a bottom side by a bottom wall 126. Side walls 124a-d are constructed of ribs 128 separated by perforations 130 and bottom wall 126 is constructed by ribs 132 separated by perforations 134. Ribs 128 of side wall 124a are offset in a lengthwise direction relative to ribs 128 of opposite side wall 124b, as shown by distance "d" in FIG. 10. Distance "d" may vary, however, in this embodiment, on average, it is approximately 0.015" to 0.030". Offsetting ribs 128 in this manner ensures that a microtome blade passing through walls 124a and 124b contacts a more uniform amount of cassette material along its length. This leads to longer blade life, more uniform blade wear and more consistent high quality slices of embedded tissue. Ribs 132 and perforations 134 extend in their lengthwise direction toward a central area 126a of bottom wall 126. In this preferred embodiment, side walls 124a-d are constructed such that the ratio of plastic cassette material, such as PFA, to the open area formed by perforations 130 is approximately 3.7:1. To achieve at least this ratio in the preferred embodiment, ribs 128 have a width W1 of approximately 0.010" to 0.014" while perforations 130 have a width W2 of approximately 0.040" to 0.050". This perforated area, which is below solid side wall portion 136 is the area which will be cut with a microtome blade after embedding of tissue sample 80 (FIG. 6). Especially when using PFA with a Shore D hardness of 48 to 55 as the material for cassette 120, in combination with the industry standard paraffin embedding material mentioned above, this ratio of cassette material to open area has been found to improve the quality of cuts made through the embedded cassette and increase blade life significantly. Depending on the respective molecular weights of the embedding material and the cassette material, this ratio may be increased or reduced.

A flange 140 surrounds the upper side of cassette body 122 and contains respective upwardly facing depressions 142a, 142b, 142c, 142d. A number of downwardly facing depressions 142e, 142f (only two of several referenced) are also contained in flange 140. These depressions respectively register with at least detents 54, 56 and 58, 60 of frame 12 (see FIGS. 3 and 5). It will be appreciated that additional lower detents may be formed on frame 12 to provide further support and prevent cassette 10 from being pushed too far through frame 12. In such a case, additional depressions are formed in the underside of flange 140 to accommodate the additional supportive detents. The depressions allow the effective outward extension of cassette body 120 from frame 12 to be increased thereby increasing the number of slices that may be taken from the embedded cassette in a microtome. This can be important in many situations in order to obtain the desired slides for pathologic examination.

Detents 144 are also formed on side walls 124a-d for retaining a lid 150 in place. Lid 150 is coupled to cassette body 122 by a hinge 152. Lid 150 is formed to be stiffer than bottom wall 126 of cassette body 122 so that lid 150 may be used to press the tissue sample against the bottom wall 126 and to press the bottom wall 126 against the rigid bottom 74 of base mold 14 (FIG. 5). Lid 150 is formed by a plurality of ribs 154 generally separated by perforations 156 and each extending in a lengthwise elongated fashion toward a central area 150a of lid 150. Lid 150 further includes side edges 158a, 158b extending lengthwise thereon and having a shallow "V" shape with a central apex 160a, 160b. Angle α (FIG. 10) is preferably about 4°. As with the first embodiment, the shape of side edges 158a, 158b complements similar shape of side walls 124a, 124b of cassette body 122. In this regard, these side walls 124a, 124b, either one of which may be the initial wall cut in the microtome, include respective apecies 162a, 162b. Respective ends 164a, 164b of lid 150 also complement the similar shape of cassette body side walls 124c, 124d to achieve a close fit of lid 150 within cassette body 122. The use of cassette 120 in the process of embedding one or more tissue samples, including the staging process within frame 12 and the embedding or molding process within base mold 14 is the same as described above with regard to FIGS. 1-8.

Figure 11:
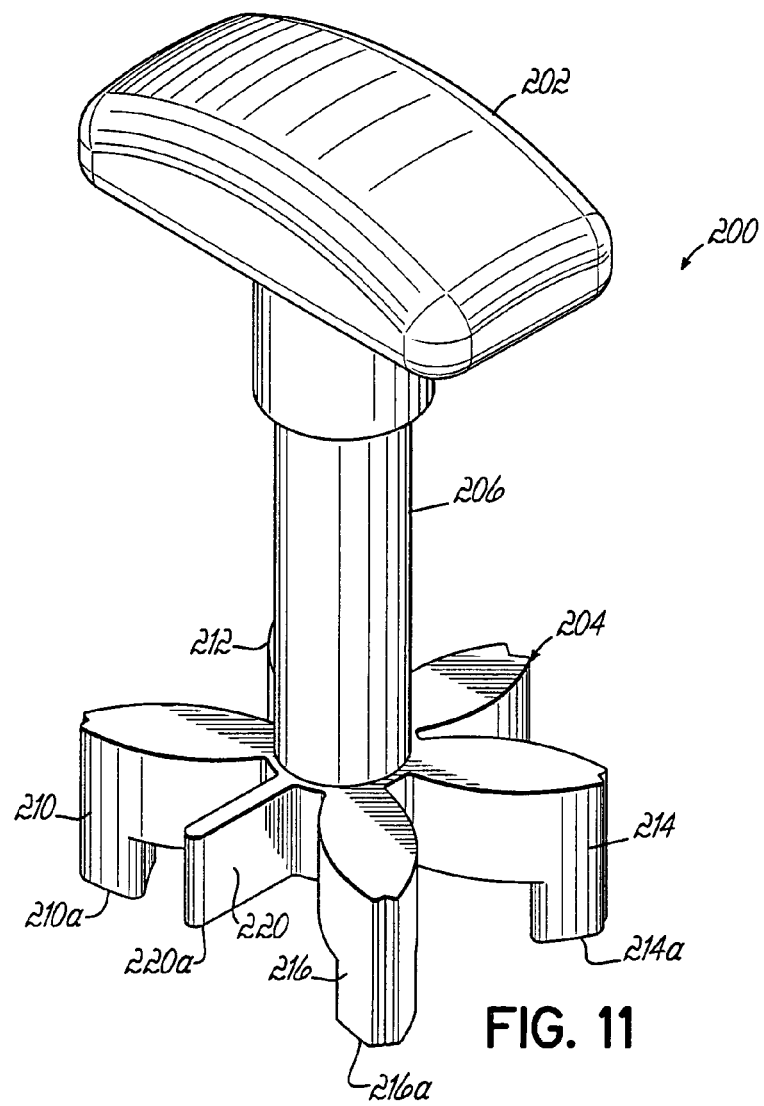
FIG. 11 is a perspective view of a manual staging device constructed in accordance with a second embodiment.
Figure 12:
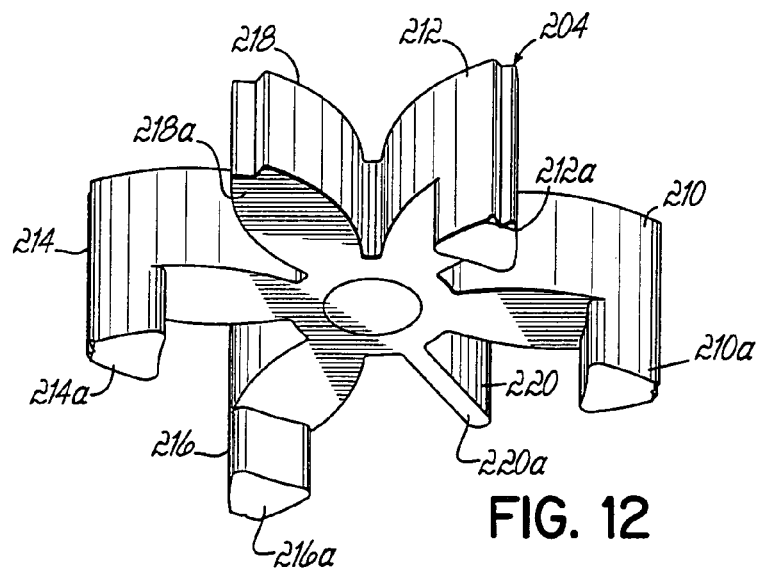
FIG. 12 is a bottom perspective view of the staging mechanism associated with the staging device of FIG. 11.

FIGS. 11 and 12 illustrate a manual staging device 200 in accordance with a second embodiment. Staging device 200 comprises an upper handle 202 and a lower staging mechanism 204 coupled together rigidly by a shaft 206. In FIG. 12, handle 202 and shaft 206 have been deleted for clarity. Staging mechanism 204 preferably comprises a plurality of four staging members 210, 212, 214, 216 extending generally radially outward from shaft 206 and each including a finger portion 210a, 212a, 214a, 216a. The finger portions 210a-216a respectively engage upper corner portions of cassette 10 (FIG. 1) or cassette 120 (FIG. 9). When the user then pushes downward on handle 202, finger portions 210a-216a urge cassette 10 or cassette 120 downward into the lower, staged position (FIG. 5). To prevent the cassette from being moved too far downward, a pair of stops 218, 220 are provided on staging mechanism 204. In this embodiment, stop surfaces 218a, 220a stop against the upper surface of frame 12 as cassette 10 or cassette 120 reaches the lower, staged position (FIG. 5). Thus, the distance between the lower ends of finger portions 210a-216a and stop surfaces 218a, 220a equates to the distance between upper detent pair 54, 56 and lower detent pair 58, 60. It will be appreciated that other forms of staging mechanisms and stops may be provided while falling within the spirit and scope of the invention.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A cassette for holding a tissue sample, comprising:
a body including a perforated bottom wall and a plurality of perforated side walls extending upwardly with respect to said bottom wall to define an interior space for receiving the tissue sample;
said bottom wall and said plurality of side walls being constructed of a material capable of being successfully sectioned in a microtome and resistant to degradation during histologic tissue processing, wherein said plurality of side walls comprise first and second side walls each having a length and extending upwardly from opposite edges of said bottom wall, at least one of said first and second side walls including portions angling toward the other of the first and second side walls on the opposite edge of the bottom wall to define an outwardly projecting portion proximate a midpoint along said length of said at least one side wall.

2. The cassette of claim 1, further comprising a lid configured to be coupled with said body and movable between open and closed positions, said lid being stiffer than said bottom wall.

3. The cassette of claim 1, wherein said plurality of side walls comprise perforated walls in which the ratio of open area to solid area is at least about 3.5:1.

4. The cassette of claim 1, wherein said plurality of side walls comprise perforated walls in which the ratio of open area to solid area is at least about 3.0:1.

5. The cassette of claim 1, wherein said plurality of side walls comprise perforated walls in which the ratio of open area to solid area is at least about 2.5:1.

6. The cassette of claim 1, wherein said first and second side walls include a length and comprise perforated walls constructed with spaced apart ribs, said ribs of said first side wall being offset along said length with respect to said ribs of said second side wall.

7. The cassette of claim 1, further comprising:
a flange extending along upper portions of at least two of said side walls, said flange including depressions configured to register with detents in a frame during a tissue embedding process.

8. The cassette of claim 1, wherein said bottom wall includes a central area and comprises a perforated wall constructed with spaced apart ribs, said ribs angling toward said central area.

* * * * *